United States Patent [19]

Kleschick et al.

[11] Patent Number: 4,983,772
[45] Date of Patent: Jan. 8, 1991

[54] 2,6-DISUBSTITUTED ANILINES

[75] Inventors: William A. Kleschick, Martinez; Mark J. Costales, Concord, both of Calif.; Robert J. Ehr, Eden Prairie, Minn.; Ben C. Gerwick, III, Clayton, Calif.; deceased Meikle, late of Walnut Creek, Calif.; by Diane L. Meikle, executrix, Alamo, Calif.; William T. Monte, Concord, Calif.; Norman R. Pearson, Walnut Creek, Calif.

[73] Assignee: The Dow Chemical Company, Midland, Mich.

[21] Appl. No.: 406,666

[22] Filed: Sep. 13, 1989

Related U.S. Application Data

[60] Division of Ser. No. 261,460, Oct. 21, 1988, Pat. No. 4,886,883, which is a division of Ser. No. 940,480, Dec. 10, 1986, Pat. No. 4,818,273, which is a continuation-in-part of Ser. No. 768,393, Aug. 22, 1985, abandoned, which is a continuation-in-part of Ser. No. 551,758, Nov. 14, 1983, abandoned.

[51] Int. Cl.$^5$ ............................................. G07C 85/11
[52] U.S. Cl. ..................................... 564/442; 546/300; 560/19; 564/440
[58] Field of Search .................... 560/19; 546/300; 564/442, 440

[56] References Cited

U.S. PATENT DOCUMENTS

| | | | |
|---|---|---|---|
| 2,659,740 | 11/1953 | Dickey | 564/442 |
| 3,162,681 | 12/1964 | Connors | 564/442 |
| 3,337,570 | 8/1967 | Sherlock | 564/442 |
| 3,503,966 | 3/1970 | Metlesics | 564/442 |
| 3,637,366 | 1/1972 | Wietelmann et al. | |
| 3,920,690 | 11/1975 | Harrington et al. | |
| 3,923,810 | 12/1975 | Harrington et al. | |
| 3,985,799 | 10/1976 | Houlihan | 71/84 |
| 4,006,185 | 2/1977 | Tobin | 564/442 |
| 4,036,840 | 7/1977 | O'Brien et al. | |
| 4,052,371 | 10/1977 | Juncle | 564/442 |
| 4,145,364 | 3/1979 | Mulvey | 560/19 |
| 4,146,718 | 3/1979 | Jenks | 564/442 |
| 4,160,764 | 7/1979 | Mischke | 560/19 |
| 4,162,322 | 7/1979 | Malen et al. | 546/233 |
| 4,173,637 | 12/1979 | Nishiyama | 546/300 |
| 4,209,464 | 6/1980 | Steinman | 564/440 |
| 4,214,004 | 7/1980 | Plummer | 560/124 |
| 4,218,373 | 8/1980 | Wolfrum et al. | |
| 4,261,926 | 4/1981 | Ross | 564/442 |
| 4,288,621 | 9/1981 | Kohn | 560/19 |
| 4,310,677 | 1/1982 | Reissenweber | 560/19 |
| 4,349,378 | 9/1982 | Cliff et al. | 71/103 |
| 4,388,472 | 6/1983 | Cartwright et al. | 71/108 |
| 4,394,521 | 2/1983 | Sappelt | 564/442 |
| 4,404,402 | 9/1983 | Ladner | 564/440 |
| 4,444,774 | 4/1984 | Dusza et al. | |
| 4,532,255 | 7/1985 | Fujii | 560/19 |
| 4,543,426 | 9/1985 | Liu | 564/442 |
| 4,605,433 | 8/1986 | Pearson et al. | |
| 4,625,062 | 11/1986 | Nagata | 564/442 |
| 4,638,075 | 1/1987 | Kleschick et al. | 71/92 |
| 4,687,855 | 8/1987 | Boger | 546/300 |
| 4,727,017 | 2/1988 | Pollet et al. | |
| 4,728,601 | 3/1988 | Rauland et al. | |
| 4,749,813 | 6/1988 | Marhold | 564/442 |
| 4,772,720 | 9/1988 | Kleschick et al. | 71/92 |
| 4,806,687 | 2/1989 | Balthazor | 564/442 |
| 4,808,752 | 2/1989 | Papenfus | 564/440 |
| 4,830,663 | 5/1989 | Dunbar | 71/92 |

FOREIGN PATENT DOCUMENTS

| | | |
|---|---|---|
| 0142811 | 5/1985 | European Pat. Off. |
| 27060 | 10/1973 | Japan |
| 951652 | 3/1964 | United Kingdom |
| 1455474 | 11/1976 | United Kingdom |

OTHER PUBLICATIONS

J. Tani et al., Chem. Pharm. Bull., 30, 3530–3543 (1982).
T. A. Emokpae et al., J. Chem. Soc. Perkin II, 1976, 14–17.
Broadbent et al., J. Chem. Soc., 1965, pp. 3369–3372.
Okabe et al., J. Fac. Agr., Kyushu University, 19, 91–102 (1975).
Okabe et al., J. Heterocyclic Chem., 20, 735 (1983).
Novinson et al., J. Med. Chem., 25, 420–426 (1982).
Burger, *Medicinal Chemistry*, 2nd Edition, Interscience (1960), p. 43.

*Primary Examiner*—Donald G. Daus
*Attorney, Agent, or Firm*—D. Wendell Osborne; Merlin B. Davey

[57] ABSTRACT

Novel substituted triazolo [1,5-a]pyrimidine-2-sulfonamides, e.g., 5,7-dimethyl-N-(2,6-dichlorophenyl)-1,2,4-triazolo[1,5-a]pyrimidine-2-sulfonamide and their agriculturally acceptable salts are prepared. These compounds and compositions containing them are useful for the control of unwanted vegetation. Novel substituted triazolo[1,5-a]pyrimidine-2-sulfonyl chlorides and substituted anilines and their use as intermediates are also described.

2 Claims, No Drawings

2,6-DISUBSTITUTED ANILINES

CROSS-REFERENCE TO RELATED APPLICATION

This application is a divisional application of application Ser. No. 261,460, filed Oct. 21, 1988, now U.S. Pat. No. 4,886,883, which is a divisional application of application Ser. No. 940,480, filed Dec. 10, 1986, now U.S. Pat. No. 4,818,273, which is a continuation-in-part of application Ser. No. 768,393, filed Aug. 22, 1985, now abandoned, which is a continuation in part of application Ser. No. 551,758, filed Nov. 14, 1983, now abandoned. The disclosure of the specification and claims of application Ser. No. 768,393 is hereby incorporated by reference.

BACKGROUND OF THE INVENTION

In recent years there has been a great deal of effort directed to the development of sulfonamides having herbicidal activity and several of these compounds have reached the stage of commercialization, i.e., chlorosulfuron and sulfometuron methyl. These compounds exhibit both preemergence and postemergence activity against undesirable vegetation and, in addition, have a low toxicity to mammals. The compounds of the prior art may be depicted as follows:

wherein Ar is usually a benzene derivative and Ar' is usually a pyrimidine or symmetrical triazine derivative.

In addition, there are a number of other sulfonamide herbicides that have been commercialized, for example, methyl sulfanilylcarbamate; O,O-diisopropyl phosphorodithioate-S-ester with N-(2-mercaptoethyl)benzenesulfonamide; 3-isopropyl-1H-2,1,3-benzothiadiazin-4(3H)-one-2,2-dioxide; N-[2,4-dimethyl-5-[[(trifluoromethyl)sulfonyl]amino]phenyl]acetamide and 3,5-dinitro-$N^4$,$N^4$-dipropylsulfanilamide.

It has now been found that novel compounds having the formula:

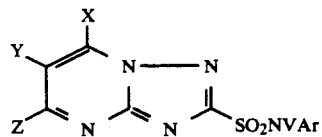

wherein

Ar represents an aromatic or heteroaromatic ring chosen from among phenyl; 1- or 2-napthyl; 2-, 3- or 4-pyridyl; 2- or 3-thienyl; 2- or 3-furyl; 2-, 4-, or 5-thiazolyl; 2-, 4-, or 5-imidazolyl; 2-, 4-, or 5-oxazolyl; 3-, 4-, or 5-isothiazolyl; 3-, 4-, or 5-isoxazolyl; 3-, 4-, or 5-pyrazolyl; 2-benzthiazolyl; 2-benzoxazolyl; 2-benzimidazolyl: or 1-benztriazolyl; and Ar is unsubstituted except in the case of where Ar is phenyl or Ar is substituted with one to five substituents chosen from among $C_1$–$C_6$ alkyl; benzyl; halo; $C_1$–$C_6$ mono- or polyhaloalkyl; phenyl; phenyl substituted with one or more groups chosen from halo, $C_1$–$C_6$ alkyl, or $C_1$–$C_6$ haloalkyl; hydroxy; $C_1$–$C_6$ alkoxy; $C_1$–$C_6$ mono- or polyhaloalkoxy; phenoxy; phenoxy substituted with one or more groups chosen from halo, $C_1$–$C_6$ alkyl or $C_1$–$C_6$ haloalkyl; 2-pyridyloxy; 2-pyridyloxy substituted with one or more groups chosen from halo, $C_1$–$C_6$ alkyl or $C_1$–$C_6$ haloalkyl; amino; $C_1$–$C_6$ alkylamino; $C_1$–$C_6$ dialkylamino; nitro; $C_1$–$C_6$ alkylthio; $C_1$–$C_6$ polyhaloalkylthio; $C_1$–$C_6$ alkylsulfinyl; $C_1$–$C_6$ polyhaloalkylsulfinyl; $C_1$–$C_6$ alkylsulfonyl; $C_1$–$C_6$ polyhaloalkylsulfonyl; phenylthio; phenylthio substituted with one or more groups chosen from halo, $C_1$–$C_6$ alkyl or $C_1$–$C_6$ haloalkyl; phenylsulfinyl; phenylsulfinyl substituted with one or more groups chosen from halo, $C_1$–$C_6$ alkyl, or $C_1$–$C_6$ haloalkyl; phenylsulfonyl; phenyl sulfonyl substituted with one or more groups chosen from halo, $C_1$–$C_6$ alkyl, or $C_1$–$C_6$ haloalkyl; cyano; carboxyl; $C_1$–$C_{10}$ alkoxycarbonyl; phenoxycarbonyl; phenoxycarbonyl substituted with one or more groups chosen from halo, $C_1$–$C_6$ alkyl or $C_1$–$C_6$ haloalkyl; alkoxyalkoxycarbonyl wherein the number of carbons in the alkoxyalkoxy fragment ranges from 2–10 and the number of oxygens in the alkoxyalkoxy fragment ranges from 2–4; 2-pyridylmethoxycarbonyl; dialkylaminoalkoxycarbonyl wherein the number of carbons in the dialkylaminoalkoxy fragment ranges from 3–10 and the number of oxygens in the dialkylaminoalkoxy fragment is one; $C_3$–$C_6$ alkenyloxycarbonyl; COON=C($R^{14}$)($R^{14}$) wherein each $R^{14}$ independently represents hydrogen, $C_1$–$C_6$ alkyl or phenyl; amino-, $C_1$–$C_6$ alkylamino-, or di $C_1$–$C_6$ alkylaminocarbonyl; $C_1$–$C_{10}$ alkoxysulfonyl; $C_1$–$C_4$ polyhaloalkoxysulfonyl; di $C_1$–$C_6$ alkylaminosulfonyl; formyl; $C_1$–$C_6$ alkylcarbonyl; $C_1$–$C_6$ mono- or polyhaloalkylcarbonyl; phenylcarbonyl; phenylcarbonyl substituted with one or more groups chosen from halo, $C_1$–$C_6$ alkyl or $C_1$–$C_6$ haloalkyl; or C($R^{15}$)($R^{15}$)O$R^{16}$ wherein each $R^{15}$ independently represents hydrogen or $C_1$–$C_6$ alkyl and $R^{16}$ represents hydrogen, $C_1$–$C_6$ alkyl, benzyl, phenylcarbonyl or $C_1$–$C_6$ alkylcarbonyl (except in the cases of thio, sulfinyl, and sulfonyl substituents where if one of these substituents is present the other one to four Ar substituents may not be chosen from among the other two; oxycarbonyl substituents where the other one to four Ar substituents may not be chosen from among different oxycarbonyl substituents; or aminocarbonyl substituents where the other one to four Ar substituents may not be chosen from among different aminocarbonyl substituents); X, Y, and Z independently represent hydroxyl; carboxyl; hydrogen; $C_1$–$C_6$ alkyl; $C_1$–$C_6$ mono- or polyhaloalkyl; $C_1$–$C_6$ alkoxy; $C_1$–$C_6$ mono- or polyhaloalkoxy; amino, $C_1$–$C_4$ alkylamino, or di $C_1$–$C_4$ alkylamino; phenyl; phenyl substituted with one or more groups chosen from halo, nitro, $C_1$–$C_6$ alkyl, or $C_1$–$C_6$ mono- or polyhaloalkyl; $C_1$–$C_6$ alkylthio; halo; or two adjacent substituents (i.e., X and Y or Y and Z) are joined together to form a five, six, or seven-membered saturated cyclic structure of carbon atoms or one said carbon atom of X,Y or Y,Z is replaced by a heteroatom chosen from among nitrogen, oxygen, or sulfur (i.e., X,Y or Y,Z is —(CH$_2$)$_n$— wherein n is 3, 4, or 5; or X,Y or Y,Z is —(CH$_2$)$_n$—A—(CH$_2$)$_m$— wherein n is 0–4, the value of m is equal to the ring size minus (n+3) and A is NH, O, or S); and V is H or R and R represents $C_1$–$C_{10}$ alkyl, $C_3$–$C_{10}$ alkenyl, $C_3$–$C_{10}$ alkynyl, phenylalkyl, $C_2$–$C_{10}$ alkanoyl, $C_1$–$C_{10}$ alkoxycarbonyl, phenoxycarbonyl, di $C_1$–$C_6$ alkylaminocarbonyl, $C_1$–$C_6$ alkylsulfonyl, phenylsulfonyl, $C_1$–$C_{10}$ alkoxythiocarbonyl or phenoxythiocarbonyl, wherein alkyl, alkenyl, alkynyl, and alkoxy in each instance is optionally substituted by halo and each phenyl moiety is optionally substituted by one or two groups selected from halo, nitro, $C_1$–$C_4$ alkyl, or $C_1$–$C_4$ haloalkyl; and, when V represents hydrogen, agriculturally acceptable salts thereof are useful pre- and post-emergence herbicides or intermediates for preparing herbicides.

Treatment of the locus of undesired vegetation or weeds with the novel compounds or with compositions containing herbicidally effective amounts of the novel compounds in admixture with one or more inert carriers can be used to obtain broad spectrum or selective weed control depending upon the specific compound and the amount applied. Broadleaf weeds are particularly susceptible to the compounds and control of undesirable vegetation in crops such as wheat, rice, corn, soybeans, and cotton can be achieved. Aquatic vegetation is controlled by the compounds.

In addition, certain novel tetrahydro derivatives of the compounds of general Formula I, which can be represented by Formula II

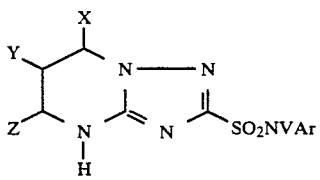

wherein X, Y, A, V, and Ar as defined hereinabove and their agriculturally acceptable salts also exhibit herbicidal activity.

The invention further encompasses certain of the novel substituted triazolo[1,5-a]pyrimidine-2-sulfonyl chlorides and certain of the novel substituted anilines which are useful in preparing the compounds of Formulae I and II.

DETAILED DESCRIPTION OF THE INVENTION

The contemplated aromatic or heteroaromatic ring systems, Ar, of Formula I include substituted or unsubstituted (except for phenyl, which must be substituted) phenyl; 1- or 2-napthyl; 2-, 3- or 4-pyridyl; 2- or 3-thienyl; 2- or 3-furyl; 2-, 4- or 5-thiazolyl; 2-, 4- or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazolyl; 2-benzimidazolyl and 1-benztriazolyl. Typical examples of substituents found on the aromatic or heteroaromatic ring systems may be one, more than one, or a combination of the following: halo, $C_1$-$C_6$ alkyl, benzyl, $C_1$-$C_6$ mono- or polyhaloalkyl, phenyl (optionally substituted with one or more groups chosen from halo, $C_1$-$C_6$ alkyl, or $C_1$-$C_6$ haloalkyl), hydroxy, $C_1$-$C_6$ alkoxy, $C_1$-$C_6$ mono- or polyhaloalkoxy, phenoxy or pyridyloxy (each optionally substituted with one or more groups chosen from halo, $C_1$-$C_6$ alkyl or $C_1$-$C_6$ haloalkyl), nitro, amino, $C_1$-$C_6$ alkylamino, di $C_1$-$C_6$ alkylamino, $C_1$-$C_6$ alkylthio, $C_1$-$C_6$ polyhaloalkylthio, $C_1$-$C_6$ alkylsulfinyl, $C_1$-$C_6$ polyhaloalkylsulfinyl, $C_1$-$C_6$ alkylsulfonyl, $C_1$-$C_6$ polyhaloalkylsulfonyl, phenylthio or phenylsulfinyl or phenylsulfonyl (each phenyl optionally substituted with one or more groups chosen from halo, $C_1$-$C_6$ alkyl, or $C_1$-$C_6$ haloalkyl), cyano, carboxylic acids and derivatives of carboxylic acids (esters derived from available alcohols and amides derived from ammonia or available primary and secondary amines, which can be termed oxycarbonyl and aminocarbonyl substituents) including $C_1$-$C_{10}$ alkoxycarbonyl, phenoxycarbonyl optionally substituted with one or more groups chosen from halo, $C_1$-$C_6$ alkyl, or $C_1$-$C_6$ haloalkyl, alkoxyalkoxycarbonyl wherein the number of carbons in the alkoxyalkoxy fragment ranges from 2-10 and the number of oxygens in the alkoxyalkoxy fragment ranges from 2-4, 2-pyridylmethoxycarbonyl, dialkylaminoalkoxycarbonyl wherein the number of carbons in the dialkylaminoalkoxy fragment ranges from 3-10 and the number of oxygens in the dialkylaminoalkoxy fragment is one, $C_3$-$C_6$ alkenyloxyoarbonyl, COON=$C(R^{14})(R^{14})$ wherein each $R^{14}$ independently represents hydrogen, $C_1$-$C_6$ alkyl, or phenyl, $C_1$-$C_{10}$ alkoxysulfonyl, $C_1$-$C_4$ polyhaloalkoxysulfonyl, amino- or $C_1$-$C_6$ alkylamino or di $C_1$-$C_6$ alkylaminocarbonyl, di $C_1$-$C_6$ alkylaminosulfonyl, formyl, $C_1$-$C_6$ alkylcarbonyl; $C_1$-$C_6$ mono- or polyhaloalkylcarbonyl, phenylcarbonyl (optionally substituted with one or more groups selected from halo, $C_1$-$C_6$ alkyl, or $C_1$-$C_6$ haloalkyl), or $C(R^{15})(R^{15})OR^{16}$ wherein each $R^{15}$ independently represents hydrogen or $C_1$-$C_6$ alkyl and represents hydrogen, $C_1$-$C_6$ alkyl, benzyl, phenylcarbonyl, or $C_1$-$C_6$ alkylcarbonyl. In cases where one substituent is a thio, sulfinyl, or sulfonyl moiety, other substituents may not be chosen from among the other two. Also, in cases where one substituent is an oxycarbonyl moiety, other substituents may not be chosen from among other oxycarbonyl moieties; and where one substituent is an aminocarbonyl moiety, other substituents may not be chosen from among other aminocarbonyl moieties. Halo in each instance represents fluoro, chloro, bromo, or iodo.

Compounds of Formula I wherein Ar represents substituted phenyl or substituted or unsubstituted 1- or 2-naphthyl; 2-, 3-, or 4-pyridyl; 2- or 3-thienyl; or 3-, 4-, or 5-pyrazolyl are preferred. Those wherein Ar represents substituted phenyl, substituted 1-naphthyl, or substituted 3-, 4-, or 5-pyrazolyl are more preferred.

In the case of the more preferred compounds of Formula I wherein Ar is substituted phenyl, Ar can be depicted as the formula $$\underset{R^5}{\underset{|}{\overset{R^2}{\overset{|}{\underset{R^4}{\bigcirc}}}}} \begin{matrix} R^1 \\ \end{matrix}$$

wherein $R^1$, $R^2$, $R^3$, $R^4$, and $R^5$ independently represent each of the Ar substituents (with each of the listed exceptions) noted in the Summary of the Invention and in the foregoing discussion, or hydrogen, provided not all are hydrogen. Of those substituents, the following are preferred. $R^1$ represents F, Cl, Br, I, —NO$_2$, phenyl, phenoxy (optionally substituted by one or more substituents selected from F, Cl, Br, I, $C_1$-$C_4$ alkyl, and $C_1$-$C_4$ haloalkyl), —CF$_3$, —OCF$_3$, —OCF$_2$CF$_2$H, —OCF$_2$CCl$_2$H, —OCH$_2$CF$_3$, —SCF$_3$, —SCF$_2$—CF$_2$H, —SCF$_2$CCl$_2$H, —SOCF$_3$, —SOCF$_2$CF$_2$H, —SOCF$_2$CCl$_2$H, —SO$_2$CF$_3$, —SO$_2$CF$_2$CF$_2$H, —SO$_2$CF$_2$CCl$_2$H, —SR$^6$, —SOR$^6$, —SO$_2$R$^6$, —CN, —COOR$^7$, —CONH$_2$, —CONHR$^8$, —CONR$^8$R$^8$, —SO$_3$R$^8$, or SO$_3$CH$_2$CF$_3$; $R^2$ and $R^4$ represent H, F, Cl, Br, I, $C_1$-$C_4$ alkyl, —COOR$^7$, or —OR$^8$; $R^3$ is H; and $R^5$ represents H, phenyl, $C_1$-$C_4$ alkyl, $C_1$-$C_4$ alkoxy, F, Cl, Br, I, —NO$_2$, —CF$_3$, —OCF$_3$, —OCF$_2$CF$_2$H, —OCF$_2$CCl$_2$H, —OCH$_2$CF$_3$, —SCF$_3$, —SCF$_2$CF$_2$H, —SCF$_2$CCl$_2$H, —SOCF$_3$, —SOCF$_2$CF$_2$H, —SOCF$_2$CCl$_2$H, —SO$_2$CF$_3$, —SO$_2$CF$_2$CF$_2$H, —SO$_2$CF$_2$CCl$_2$H, —SR$^6$, —SOR$^6$, —SO$_2$R$^6$, —CN, —COOR$^7$, —CONH$_2$, —CONHR$^8$, —CONR$^8$R$^8$, —SO$_3$CH$_2$CF$_3$, or —CR$^6$R$^6$OR$^6$, wherein R$^6$ represents H or C$_1$–C$_4$ alkyl, R$^7$ represents C$_1$–C$_6$ alkyl, C$_3$–C$_4$ alkenyl, C$_3$–C$_4$ alkynyl, C$_1$–C$_4$ alkoxy C$_2$–C$_3$ alkyl, phenyl (optionally substituted by one or two substituents selected from F, Cl, Br, I, C$_1$–C$_4$ alkyl, and C$_1$–C$_4$ haloalkyl), or 2-pyridylmethyl and R$^8$ represents C$_1$–C$_4$ alkyl.

Compounds of Formula I in which Ar is represented by the formula

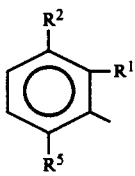

wherein R$^1$ represents C$_1$–C$_4$ alkyl, F, Cl, Br, I, —NO$_2$, —SR$^6$, —SOR$^6$, —SO$_2$R$^6$, —COOR$^7$, or —CF$_3$; R$^2$ represents H, F, Cl, Br, I, C$_1$–C$_4$ alkyl, or —COOR$^7$ and R$^5$ represents H, C$_1$–C$_4$ alkyl, C$_1$–C$_4$ alkoxy, F, Cl, Br, I, —CH$_2$OR$^6$, phenyl, —NO$_2$, or —COOR$^7$, wherein R$^6$ represents C$_1$–C$_4$ alkyl and R$^7$ represents C$_1$–C$_4$ alkyl, C$_3$–C$_4$ alkenyl, C$_3$–C$_4$ alkynyl, 2-ethoxyethyl or 2-pyridylmethyl are most especially preferred.

In the case of the more preferred compounds of Formula I wherein Ar represents 3-, 4-, or 5-pyrazolyl, Ar can be depicted as the formula

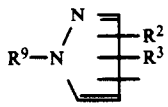

wherein R$^2$ and R$^3$ independently represent each of the substituents (with each of the listed exceptions) noted in the Summary of the Invention and in the foregoing discussions and R$^9$ represents hydrogen or C$_1$–C$_6$ alkyl. Preferred compounds of this type include those wherein R$^2$ and R$^3$ each independently represents H, C$_1$–C$_4$ alkyl, benzyl, F, Cl, Br, I, NO$_2$, CF$_3$, OCF$_3$, C$_1$–C$_4$ alkoxy, C$_1$–C$_{10}$ alkoxycarbonyl, C$_3$–C$_6$ alkenyloxycarbonyl, benzyloxycarbonyl, or amino-, C$_1$–C$_4$ alkylamino- or di C$_1$–C$_4$ alkylaminocarbonyl.

The substituents on the triazolopyrimidine fragment of Formula I are represented by X, Y, and Z. Substituents X, Y, and Z independently represent hydroxyl, carboxyl, hydrogen, C$_1$–C$_6$ alkyl, C$_1$–C$_6$ mono- or polyhaloalkyl, C$_1$–C$_6$ alkoxy, C$_1$–C$_6$ mono- or polyhaloalkoxy, amino, C$_1$–C$_4$ alkylamino, di C$_1$–C$_4$ alkylamino, phenyl (optionally substituted with one or more groups chosen from F, Cl, Br, I, nitro, C$_1$–C$_6$ alkyl, or C$_1$–C$_6$ mono- or polyhaloalkyl), C$_1$–C$_6$ alkylthio, halogen, or two adjacent substituents (i.e. X and Y or Y and Z) are joined together to form a saturated five, six, or seven-membered saturated cyclic structure of carbon atoms or up to one heteroatom chosen from among nitrogen, oxygen, or sulfur (i.e. X,Y or Y,Z is —(CH$_2$)$_n$— wherein n is 3, 4, or 5; or X,Y or Y,Z is —(CH$_2$)$_n$—A—(CH$_2$)$_m$— wherein n is 0–4, the value of m is equal to the ring size minus (n+3) and A is NH, O, or S).

Compounds of Formula I wherein X, Y, and Z independently represent H, F, Cl, Br, I, C$_1$–C$_4$ alkyl, C$_1$–C$_4$ alkoxy, C$_1$–C$_4$ alkylthio, C$_1$–C$_4$ haloalkyl are preferred.

The most highly preferred compounds of the invention are those compounds of Formula I wherein X represents H, CH$_3$, CF$_3$, OCH$_3$, OC$_2$H$_5$, or SCH$_3$; or Y represents H, Cl, or CH$_3$; or Z represents H, CH$_3$, or OCH$_3$; and Ar represents substituted phenyl wherein R$^1$ represents F, Cl, Br, CF$_3$, NO$_2$, or C$_1$–C$_4$ alkoxycarbonyl; or R$^2$ represents H or CH$_3$; or R$^5$ represents H, F, Cl, Br, OCH$_3$, or CH$_3$; and R$^3$ and R$^4$ represent hydrogen and their agriculturally acceptable salts. Additional most highly preferred compounds are those compounds of Formula I wherein X or Y or E are as defined above and Ar represents 3-, 4-, or 5-pyrazolyl wherein R$^9$ represents H, CH$_3$, or C$_2$H$_5$; or R$^2$ and R$^3$ independently represent H, CH$_3$, CF$_3$, or C$_1$–C$_4$ alkoxycarbonyl and their agriculturally acceptable salts.

The substituent V of Formulae I and II represents any of the following: hydrogen, alkyl, alkenyl, alkynyl, phenylalkyl, substituted phenylalkyl, alkanoyl, alkoxycarbonyl, phenoxycarbonyl, dialkylaminocarbonyl, alkylsulfonyl, phenylsulfonyl, alkylthiocarbonyl, or phenylthiocarbonyl wherein alkyl, alkenyl, and alkynyl are as defined above and each phenyl group is optionally substituted as defined above.

Preferred derivatives of the invention are those compounds of Formula I wherein V represents hydrogen, C$_1$–C$_4$ alkyl, allyl, benzyl, —COR$^{13}$, —CO$_2$R$^{13}$, —CONR$^{13}$R$^{13}$, —CSOR$^{13}$, and —SO$_2$R$^{13}$, wherein R$^{13}$ is C$_1$–C$_6$ alkyl, phenyl (optionally substituted by one or more groups chosen from halo, C$_1$–C$_6$ alkyl, or C$_1$–C$_6$ haloalkyl), or C$_1$–C$_2$ haloalkyl.

The more preferred derivatives of the invention with respect to V are those wherein V represents hydrogen, C$_1$–C$_4$ alkyl, allyl, benzyl, C$_2$–C$_4$ alkanoyl, C$_2$–C$_3$ haloalkanoyl, benzoyl, C$_1$–C$_4$ alkoxycarbonyl, phenoxycarbonyl, di C$_1$–C$_4$ alkylaminocarbonyl, C$_1$–C$_4$ alkoxythiocarbonyl, C$_1$–C$_4$ alkylsulfonyl, C$_1$–C$_2$ haloalkylsulfonyl, or phenylsulfonyl, each phenyl optionally substituted by one or more groups chosen from among halo, nitro, methyl, and trifluoromethyl. The most preferred compounds in this alkanoyl, C$_1$–C$_4$ alkoxycarbonyl, or di C$_1$–C$_4$ alkylaminocarbonyl.

Substituted 1,2,4-triazolo[1,5-a]pyrimidine-2-sulfonamides and their tetrahydro derivatives behave as acids due to the presence of a sulfonamide moiety proton and consequently form salts when treated with bases. The term "agriculturally acceptable salts" is employed in this application to denote compounds wherein the acidic sulfonamide proton of the compounds of Formulae I and II and replaced by a cation which is not herbicidal, especially to crop plants, nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula

wherein R$^{10}$, R$^{11}$, and R$^{12}$ each, independently represents 30 hydrogen or C$_1$–C$_{12}$ alkyl, C$_3$–C$_{12}$ cycloalkyl, or C$_3$–C$_{12}$ alkenyl, each of which is optionally substituted by one or more hydroxy, C$_1$–C$_8$ alkoxy, C$_1$–C$_8$ alkylthio or phenyl groups. Additionally, any two of R$^{10}$, R$^{11}$, and R$^{12}$ together represent an aliphatic difunctional moiety containing 1 to 12 carbon atoms and up to two oxygen or sulfur atoms. Sodium, potassium, ammonium, and triethanolaminium are most preferred cations.

Specifically preferred compounds include the compounds of Formula I given in the following examples and, except for examples 38 and 39, their agriculturally acceptable salts.

1. 5,7-Dimethyl-N-(2,6-dichlorophenyl)-1,2,4-triazolo[1,5-a]pyrimidine-2-sulfonamide
2. 5-Methyl-N-(2,6-dichlorophenyl)-1,2,4-triazolo[1,5-a]pyrimidine-2-sulfonamide
3. 5-Methyl-N-(2-bromo-6-chlorophenyl)-1,2,4-triazolo[1,5-a]pyrimidine-2-sulfonamide
4. 5-Methyl L (2,6-difluoro-3-methylphenyl)-1,2,4-triazolo[1,5-a]pyrimidine-2-sulfonamide
5. 5-Methyl-N-(2,6-difluorophenyl)-1,2,4-triazolo[1,5-a]pyrimidine-2-sulfonamide
6. 5,7-Dimethoxy-N-(2,6-dichloro-3-methylphenyl)-1,2,4-triazolo[1,5-a]pyrimidine-2-sulfonamide
7. 5,7-Dimethoxy-N-(2-methoxy-6-trifluoromethylphenyl)-1,2,4-triazolo[1,5-a]pyrimidine-2-sulfonamide
8. 5-Methyl-7-methylthio-N-(2,6-dichlorophenyl)-1,2,4-triazolo[1,5-a]pyrimidine-2-sulfonamide
9. 5-Methyl-7-methylthio-N-(2-trifluoromethylphenyl)-1,2,4-triazolo[1,5-a]pyrimidine-2-sulfonamide
10. 7-Ethoxy-5-methyl-N-(2,6-dichloro-3-methylphenyl)-1,2,4-triazolo[1,5-a]pyrimidine-2-sulfonamide
11. 5,7-Dimethyl-N-(2-chloro-6-phenylphenyl)-1,2,4-triazolo[1,5-a]pyrimidine-2-sulfonamide
12. 5-Methyl-N-(2-methyl-6-nitrophenyl)-1,2,4-triazolo[1,5-a]pyrimidine-2-sulfonamide
13. 5-Methyl-N-(2-chloro-6-methylphenyl)-1,2,4-triazolo[1,5-a]pyrimidine-2-sulfonamide
14. 6-Methyl-N-(2-bromo-6-methylphenyl)-1,2,4-triazolo[1,5-a]pyrimidine-2-sulfonamide
15. 6-Methyl-N-(2-fluoro-6-chlorophenyl)-1,2,4-triazolo[1,5-a]pyrimidine-2-sulfonamide
16. 6-Methyl-N-(2-chloro-6-methylphenyl)-1,2,4-triazolo[1,5-a]pyrimidine-2-sulfonamide
17. 6-Methyl-N-(2-methyl-6-nitrophenyl)-1,2,4-triazolo[1,5-a]pyrimidine-2-sulfonamide
18. 7-Ethoxy-5-methyl-N-(2-trifluoromethylphenyl)-1,2,4-triazolo[1,5-a]pyrimidine-2-sulfonamide
19. 7-Methoxy-5-methyl-N-(2,6-dichloro-3-methylphenyl)-1,2,4-triazolo[1,5-a]pyrimidine-2-sulfonamide
20. 7-Ethoxy-5-methyl-N-(2-bromo-6-chloro-3-methylphenyl)-1,2,4-triazolo[1,5-a]pyrimidine-2-sulfonamide
21. 5,7-Dimethoxy-N-(2,6-dibromo-3-methylphehyl)-1,2,4-triazolo[1,5-a]pyrimidine-2-sulfonamide.
22. Methyl 3-methyl-N-(5,7-dimethyl-1,2,4-triazolo[1,5-a]pyrimidine-2-sulfonyl)anthranilate.
23. Methyl 3-methyl-N-(7-ethoxy-5-methyl-1,2,4-triazolo[1,5-a]pyrimidine-2-sulfonyl)anthranilate.
24. Methyl 3-fluoro-N-(6-chloro-1,2,4-triazolo[1,5-a]pyrimidine-2-sulfonyl)anthranilate.
25. 5,7-Dimethoxy-N-(2,6-dichlorophenyl)-1,2,4-triazolo[1,5-a]pyrimidine-2-sulfonamide.
26. 7-Methyl-N-(2,6-dichlorophenyl)-1,2,4-triazolo[1,5-a]pyrimidine-2-sulfonamide.
27. N-(2,6-dichlorophenyl)-1,2,4-triazolo[1,5-a]pyrimidine-2-sulfonamide.
28. 7-Ethoxy-5-methyl-N-(2,6-dibromo-3-methylphenyl)-1,2,4-triazolo[1,5-a]pyrimidine-2-sulfonamide.
29. 6-Chloro-N-(2,6-difluorophenyl)-1,2,4-triazolo-[1,5-a]pyrimidine-2-sulfonamide.
30. 5-Methyl-7-trifluoromethyl-N-(2-methoxy-6-trifluoromethylphenyl)-1,2,4-triazolo[1,5-a]pyrimidine-2-sulfonamide.
31. 5,7-Dimethyl-N-(1,3-dimethyl-5-trifluoromethyl-4-pyrazolyl)-1,2,4-triazolo[1,5-a]pyrimidine-2-sulfonamide.
32. 5-Methyl-N-(1,3-dimethyl-5-trifluoromethyl-4-pyrazolyl)-1,2,4-triazolo[1,5-a]pyrimidine-2-sulfonamide.
33. 5,7-Dimethyl-N-(1-methyl-4-ethoxycarbonyl-4-pyrazolyl)-1,2,4-triazolo[1,5-a]pyrimidine-2-sulfonamide.
34. 5,7-Dimethoxy-N-(2-chloro-1-naphthyl)-1,2,4-triazolo[1,5-a]pyrimidine-2-sulfonamide.
35. 5-Methyl-N-(2-chloro-1-naphthyl)-1,2,4-triazolo[1,5-a]pyrimidine-2-sulfonamide.
36. 5-Methyl-7-methoxy-N-(2-chloro-1-naphthyl)-1,2,4triazolo[1,5-a]pyrimidine-2-sulfonamide.
37. 5-Methyl-7-ethoxy-N-(2-chloro-1-naphthyl)-1,2,4triazolo[1,5-a]pyrimidine-2-sulfonamide.
38. 5-Methyl-N-(2-methylpropanoyl)-N-(2,6-difluorophenyl)-1,2,4-triazolo[1,5-a]pyrimidine-2-sulfonamide.
39. 5-Methyl-N-acetyl-N-(2,5-dichlorophenyl)-1,2,4-triazolo[1,5-a]pyrimidine-2-sulfonamide.

Specially preferred compounds of Formula II include the following and their agriculturally acceptable salts:

1. 5,7-Dimethyl-N-(2,6-dichlorophenyl)-4,5,6,7-tetrahydro-1,2,4-triazolo[1,5-a]pyrimidine-2-sulfonamide
2. 5-Methyl-N-(2,6-dichlorophenyl)-4,5,6,7-tetrahydro-1,2,4-triazolo[1,5-a]pyrimidine-2-sulfonamide
3. 5,7-Dimethyl-N-(2-trifluoromethylphenyl)-4,5,6,7-tetrahydro-1,2,4-triazolo[1,5-a]pyrimidine-2-sulfonamide Furthermore, in the compounds corresponding to general Formula II, the existence of stereoisomerism is possible. For example, stereoisomeric relationships exist when at least one of substituents X, Y, and Z does not equal hydrogen. When only one of substituents X, Y, and Z does not equal hydrogen, the compound of Formula II may exist as a mixture of enantiomers. One enantiomer will be designated as having the R-configuration and the other will be designated as having the S-configuration. Each enantiomer may exhibit different levels of herbicidal activity. When two or more of substituents X, Y, or Z in Formula II do not equal hydrogen, the material may exist as a mixture of diastereomers. For example, when two substituents among X, Y and Z do not equal hydrogen, the compound may exist as two diastereomers. When all three of substituents X, Y and Z do not equal hydrogen the compound may exist as four diastereomers. In addition all of the diastereomers described above exist as a mixture of two enantiomers. All of the stereoisomers described above, diastereomers and their enantiomeric pairs, may exhibit different levels of herbicidal activity.

The synthesis of compounds of general Formula I can be carried out in a straightforward manner as illustrated in Scheme I. Reaction of a sulfonyl chloride of Formula IV with the appropriate aromatic (substituted or unsubstituted) or heteroaromatic (substituted or unsubstituted) amino compound (ArNH$_2$) under basic conditions yields the desired product of Formula I. A wide range of solvents may be employed (i.e., CH₂Cl₂, CH₃CN or pyridine) at temperatures ranging from 0° C. to reflux. Bases which serve as catalysts include pyridine, 4-dimethylaminopyridine and tertiary alkylamines such as triethylamine or N-methylmorpholine. Generally the amino compound serves as the limiting reagent. Molar ratios of between 1.1 and 1.0 for the sulfonyl chloride to amino compound and molar ratios of between 5.0 and 1.1 for the base to amino compound are used most often. A wide range of concentrations may be employed (i.e., 0.1–5M). Generally concentrations in the range of 0.5–2M are used to give a homogeneous reaction which proceeds at a convenient rate. In addition it is sometimes advantageous to use a combination of pyridine derived base catalysts and tertiary amine bases. The use of pyridine as a solvent is convenient as reaction mixture is generally maintained between −20° C. and 25° C. during the course of the chlorine addition. Most preferably, temperature ranges between −20° C. and 0° C. are employed to minimize unwanted side reactions such as hydrolysis of the compound of Formula IV to the corresponding sulfonic acid. Alternatively, the mercaptan of Formula V may be suspended in a two phase system of aqueous acid (i.e., HCl) and an organic solvent (i.e., CH₂Cl₂) and treated with sodium hypochlorite. This serves to convert the mercaptan to the sulfonyl chloride in a reproducibly good yield. The solubility of the product in the organic phase serves to protect it from hydrolysis to the sulfonic acid. Again, temperatures in the range of −20° C. to 25° C. are employed with temperatures in the range of −5° C. to 5° C. being most generally used.

SCHEME I

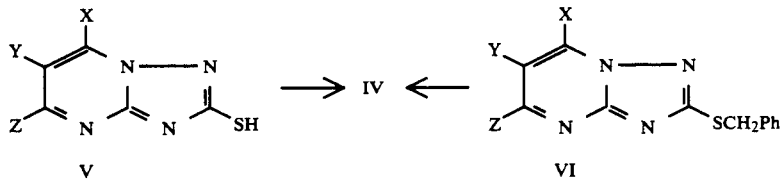

the pyridine can serve both as the solvent and the catalyst in the transformation.

SCHEME I

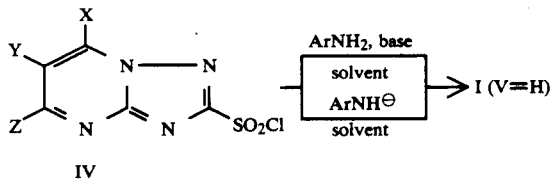

An alternative route to compounds of Formula I is also illustrated in Scheme I. In cases where the amino compound (ArNH₂) is less reactive (less nucleophic) is it advantageous to prepare a metal derivative of the amino compound by treatment with a strong base. The metal derivatives are generally prepared in ether solvents (i.e., THF) using strong bases such as alkali metal alkyls (i.e., n-BuLi) or alkali metal hydrides (i.e., NaH or KH) at temperatures ranging from −80° C. to 0° C. The amide anion thus generated in situ can be reacted with a sulfonyl chloride of Formula IV to yield the desired product of Formula I. Generally, molar ratios of the starting amino compound to sulfonyl chloride of 2 to 3 are used to ensure complete reaction.

The method of U.S. application Ser. No. 795,818, filed on Nov. 11, 1985, which method employs the condensation of N-trialkylsilylanilines with sulfonyl chlorides of Formula IV to produce compounds of Formula I, can also be used and is especially valuable in laboratory operations.

Sulfonyl chlorides of Formula IV represent key intermediates in the synthesis of sulfonamides of Formula I. Sulfonyl chlorides of Formula IV may be prepared according to routes outlined in Scheme II. Mercaptans of Formula V may be converted to sulfonyl chlorides of Formula IV by treatment with chlorine in an aqueous acidic medium. Generally the medium would be aqueous acetic acid or aqueous HCl. The temperature of the As an alternative, it is sometimes preferred to prepare sulfonyl chlorides of Formula IV from benzyl sulfides of Formula VI (Scheme II). Reaction conditions as described above for the conversion of mercaptans to sulfonyl chlorides are operable. This procedure yields by-products containing benzyl residues which are generally removed by washing the product with water and/or an appropriate organic solvent and drying in vacuo.

Compounds of general Formulae V or VI may be prepared by routes illustrated in Scheme III. Some derivatives of Formulae V and VI are known materials (i.e., V: X=Z=Me,Y=H and VI: X=Z=Me,Y=H) prepared by methods described in J. Med. Chem., 25, 420 (1982). Compounds of Formula V are prepared directly by reaction of a 1,3-diketone with commercially available 3-amino-5-mercapto-1,2,4-triazole of Formula VII in glacial acetic acid as a solvent. Generally the reaction is performed at reflux. Alternatively, the compound of Formula VII may be benzylated with benzyl chloride using an alkali earth metal alkoxide (i.e., NaOH) as a base to yield the known benzyl sulfide of Formula VIII (J. Heterocycl. Chem., 12, 1187 (1975)). The benzyl sulfide of Formula VIII can be condensed with not only 1,3-diketones but also β-keto esters, malonic esters, malonaldehyde, β-ketoaldehydes or α-formyl esters or derivatives thereof (i.e., acetals or enol ethers) to yield products of Formula VI as illustrated in Table A. Generally these reactions can be carried out under acidic conditions (i.e., glacial acetic acid as a solvent) or basic conditions (i.e., NaOR in ROH wherein R is C₁ to C₄ alkyl). In cases where the X, Y and Z substituents in Formula VI are derived from a 1,3-diketone, compounds of Formula VI may be prepared by benzylation of a compound of Formula V using an appropriate base (i.e., NaOH) and benzyl chloride in a variety of solvents (i.e., water, methanol, ethanol, THF, dioxane, acetonitrile, DMF or DMSO or combinations of the aforementioned).

SCHEME III.

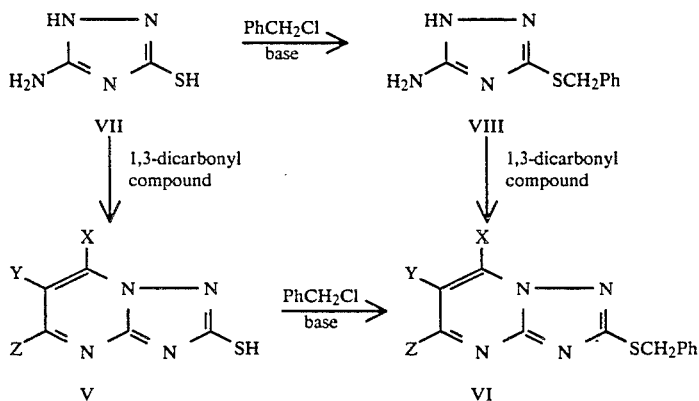

TABLE A

| 1,3-Dicarbonyl Compound or Derivative | Reaction Conditions | Compound of Formula V or VI | | |
|---|---|---|---|---|
| | | X | Y | Z |
| R-CO-CHR'-CO-R'' | acid | R | R' | R'' |
| R-CO-CHR'-CH(OR)$_2$ | acid | H | R' | R |
| R-CO-CHR'-CH(OR)$_2$ | base | R | R' | H |
| R-CO-CHR'-COOR | acid | OH* | R' | R |
| (RO)$_2$CH-CH$_2$-CH(OR)$_2$ | acid | H | H | H |
| RO$_2$C-CHR'-CO$_2$R | base | OH | R' | OH |

*In this structural representation, as well as others bearing OH groups at 5- or 7-positions of the 1,2,4-triazolo[1,5-a]pyrimidine, the enol form has been depicted. Clearly this is the equilibrium with the various keto forms.

In instances where the 1,3-dicarbonyl compound is unsymmetrical, the possibility of obtaining two different isomers from condensation with Compound VIII exists. In general, under acidic conditions the exocyclic nitrogen in Compound VIII is the first to condense with the 1,3-dicarbonyl compound. Under basic conditions the endocyclic nitrogen in Compound VIII is sometimes more reactive. Consequently, in situations where a clear difference in reactivity of the two carbonyl functionalities in the 1,3-dicarbonyl compound exists, some measure of regiochemical control may be achieved by choice of reaction conditions (i.e., entries 2 and 3 in Table I).

To prepare the alternative regioisomer to that depicted in entry 4 in Table A (i.e., VI: X=R, Y=R', and Z=OH) a route illustrated in Scheme IV was followed. Compound VIII was condensed with 2,3-dibromoalkylcarboxylic acid esters to yield a compound of Formula VI (VI: X=R, Y=R', Z=OH). The reaction is generally carried out in refluxing pyridine.

SCHEME IV.

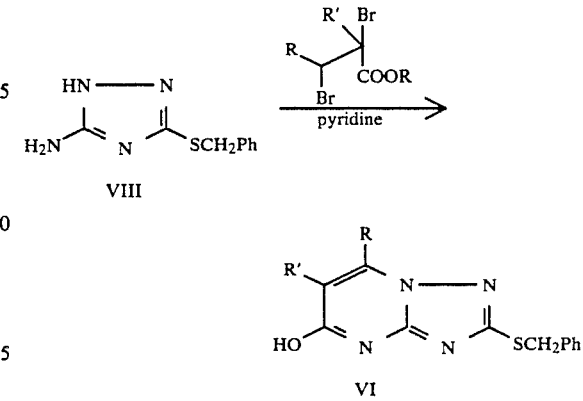

An additional route to compounds of Formula VI involves condensation of Compound VIII with methanaminium compounds of Formula IX as illustrated in Scheme V. The condensation is usually carried out by reaction in refluxing glacial acetic acid and is useful in the synthesis of a number of 6-substituted 1,2,4-triazolo[1,5-a]pyrimidines.

SCHEME V.

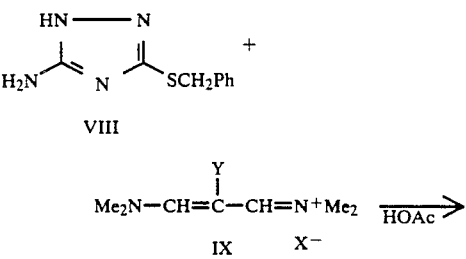

-continued
SCHEME V.

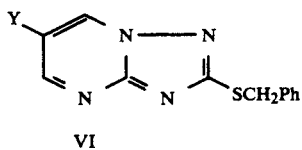
VI

In the synthetic routes listed above, compounds of Formula VI where X and/or Z is OH are capable of undergoing further transformation (Scheme VI). For example, treatment of a compound of Formula VI (X and/or Z=OH) with phosphorus oxychloride yields the corresponding compound of Formula VI (X and/or Z=Cl). The reaction is generally carried out at reflux in neat phosphorus oxychloride or with phosphorous oxychloride in a solvent (i.e., acetonitrile). Compounds of Formula VI (X and/or Z=Cl) can be further reacted with nucelophiles (i.e., NaOCH$_3$, MeMgBr) to yield compounds of Formula VI (X and/or Z=OCH$_3$ or CH$_3$, respectively). In addition, compounds of Formula VI (X and/or Z=Cl) may be reduced to afford other compounds of Formula VI (X and/or Z=H). An effective reducing agent for this type of transformation is zinc-copper couple in the presence of acid.

SCHEME VI.

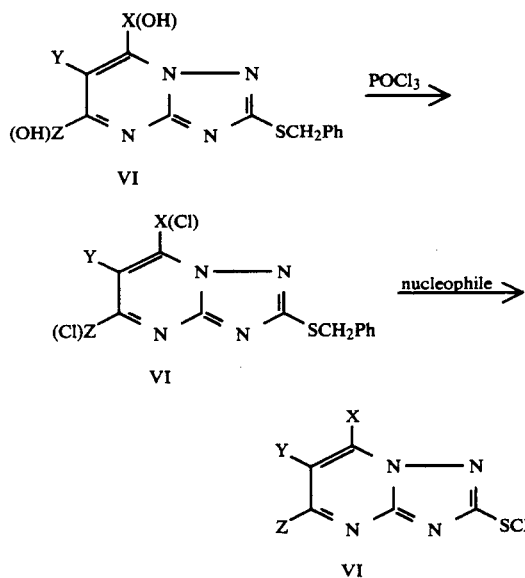

Other compounds of the present invention are best prepared in a manner illustrated in Scheme VII. Compounds such as are represented by Formula XI wherein $X^1$ and $Z^1$ are independently represented by hydrogen, $C_1$–$C_4$ alkyl, alkylthio, arylthio, or amino (including monoand disubstituted alkylamino), can be prepared by this method. The method involves the reaction of a compound of Formula X wherein X and Z independently represent hydrogen, $C_1$–$C_4$ alkyl or an appropriate leaving group with a nucleophile in a suitable solvent. This procedure effects the substitution of the leaving group by the nucleophilic unit. A representative leaving group that is effective in this process is trifluoroethoxide (—OCH$_2$CF$_3$). Representative nucleophiles for this process include alkali metal salts of alkyl mercaptans, alkali metal salts of aryl mercaptans, ammonia, primary and secondary alkylamines, and alkali metal salts of hydroxides. These nucleophiles result in the displacement of the leaving group (X and/or Z) in Formula X to produce a compound of Formula XI containing $X^1$ and/or $Z^1$ represented as alkylthio, arylthio, amino, mono- and disubstituted alkylamino, or hydroxyl, respectively. Suitable solvents for this transformation include polar aprotic solvents (i.e., DMSO, DMF), alcohols and water. Suitable reaction temperatures range from 0° C. to 100° C. although the temperature of the reaction is usually not critical. Reaction temperatures of 20° C. to 30° C. are most frequently employed.

SCHEME VII.

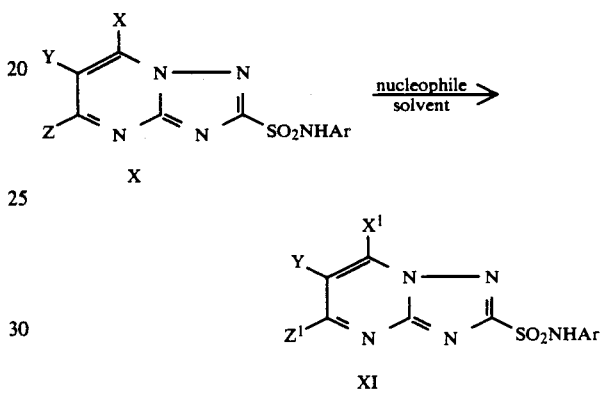

In addition certain compounds of the present invention containing a halogen in the 6-position on the 1,2,4-triazolo[1,5-a]pyrimidine ring system may be prepared by halogenation of the corresponding 6-unsubstitued compound. This is illustrated in Scheme VIII. In general, N-halo-succinimide derivatives are the halogenating agents of choice. The reactions are often performed in acid solvents at temperatures ranging from room temperature to 150° C.

SCHEME VIII

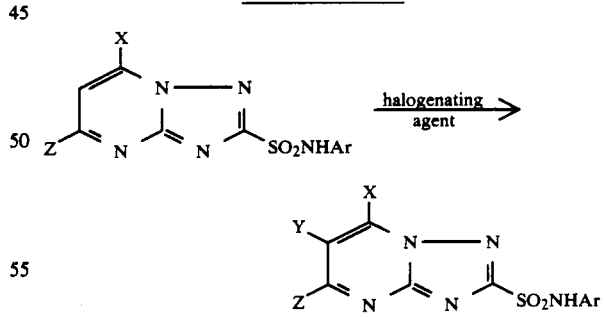

Y = halogen

Another method to prepare the compounds of the present invention is illustrated in Scheme IX. Compounds of general Formula I can be oxidized to yield compounds of Formula XII. Oxidizing agents capable of this transformation include various transition metal oxidants such as derivatives of hexavalent chromium (Cr$^{VI}$) or heptavalent manganese (Mn$^{VII}$), organic peracids or peroxides. Oxidizing agents such as potassium permanganate, chromium trioxide, peracetic acid and hydrogen peroxide are frequently employed. Preferred conditions for the conversion of compounds of Formula I to compounds of Formula XII involve reaction of the former with two to five molar equivalents of potassium permanganate in 0.1N to 1.0N aqueous alkali metal hydroxide (i.e., NaOH or KOH) as a solvent. The reaction may be run at temperatures ranging from ambient temperature to reflux. Most commonly the reaction is run at 50° C. to 60° C. The product of this reaction (Formula XII) can be hydrolyzed to a compound of Formula XIII by treatment with aqueous acid in an organic co-solvent. Typical acids include hydrochloric acid, sulfuric acid, acetic acid, trifluoroacetic acid or methanesulfonic acid. Appropriate organic co-solvents include acetone, methyl ethyl ketone, ethanol, acetonitrile or tetrahydrofuran. Lastly, compounds of Formula XIII can be reconverted to a compound of general Formula I by cyclization with a 1,3-dicarbonyl compound or an equivalent of a 1,3-dicarbonyl compound. The conditions for this cyclization, the structural requirements for the 1,3-dicarbonyl compound or an equivalent and structural considerations for the product are as described previously for the conversion of compounds of Formulae VII and VIII to compounds of Formula V and VI.

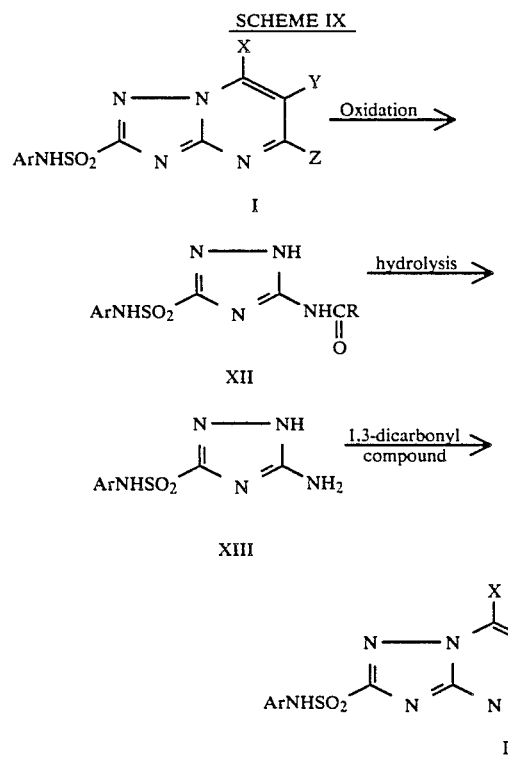

The method for the preparation of compounds of Formula I as illustrated in Scheme IX is employed advantageously in certain situations. Various functional groups present on the 1,2,4-triazolo[1,5-a]pyrimidine ring system (X, Y and Z) of Formula I which impart useful herbicidal activity can only be produced in low yield by previously described routes. The primary cause for the low yield in the previously described routes is the incompatability of the function group or the ring system which bears the functional group to the conditions required to form the required sulfonyl chlorides of Formula IV. Examples of substituents (X, Y and Z) present in compounds of Formula I which are advantageously prepared by the method outlined in Scheme IX include H, halo (F, Cl, Br and I), hydroxy, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ mono- or polyhaloalkyl, $C_1$-$C_4$ mono- or polyhaloalkoxy, $C_1$-$C_4$ polyhaloalkylthio, $C_1$-$C_4$ polyhaloalkylsulfinyl, $C_1$-$C_4$ polyhaloalkylsulfonyl, amino, $C_1$-$C_4$ mono- or dialkylamino, phenyl, substituted phenyl, phenoxy, substituted phenoxy, phenylthio, phenylsulfinyl, phenylsulfonyl, substituted phenylthio, substituted phenylsulfinyl, substituted phenylsulfonyl, carboxyl, and carboxyl derivatives such as esters derived from $C_1$-$C_4$ alcohols. The substituents X and Y or Y and Z can also be joined to form a ring containing a total of five to seven atoms. This ring may contain heteroatoms (i.e., nitrogen, oxygen or sulfur), unsaturation (i.e., —CO— or —C=C—) or a halogen substituent.

The compounds of Formula I which are most advantageously prepared by the method outlined in Scheme IX contain substituents (X, Y and Z) which are one or more of the following: H, halo (F, Cl, Br and I), $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ mono- or polyhaloalkyl, $C_1$-$C_4$ mono- or polyhaloalkoxy, $C_1$-$C_4$ polyhaloalkylthio, $C_1$-$C_4$ polyhaloalkylsulfinyl, $C_1$-$C_4$ polyhaloalkylsulfonyl, amino and $C_1$-$C_4$ mono- or dialkylamino.

Specifically preferred substituent patterns of Formula I which may be prepared by the method outlined in Scheme IX are the following:
1. X=Y=Z=H
2. X=CF$_3$, Y=H and Z=CH$_3$
3. X=Z=CF$_3$ and Y=H
4. X=Cl, Y=H and Z=CH$_3$
5. X=OCH$_3$, Y=H and Z=CH$_3$
6. X=OC$_2$H$_5$, Y=H and Z=CH$_3$
7. X=SCH$_3$, Y=H and Z=CH$_3$ The starting material of Formula I in the reaction sequence of Scheme IX may contain one or more of the following substituents: H, halo (F, Cl, Br and I) and $C_1$-$C_4$ alkyl. The aromatic ring in these starting materials and intermediates is defined as described previously for Formula I. The R group in intermediates of Formula XII may be H or CH$_3$.

Compounds of the present invention represented by Formula I wherein V is R are derived from compounds represented by Formula I wherein V is H as illustrated in Scheme X. The derivatization procedure involves treatment of compounds of Formula I wherein V is H with a base in a suitable solvent followed by the introduction of an appropriate electrophilic derivatizing reagent. From this process compounds of Formula I wherein V is R can be isolated in good yields. Suitable bases include tertiary alkylamines (i.e., triethylamine), pyridine, 4-dimethylaminopyridine, alkali metal carbonate (i.e., sodium carbonate or potassium carbonate) and alkali metal alkoxides (i.e., sodium ethoxide or potassium t-butoxide). Suitable solvents include ethers (i.e., tetrahydrofuran), pyridine, acetone, acetonitrile, alcohols (i.e., methanol, ethanol, isopropanol and t-butanol) and polar aprotic solvents (i.e., DMSO and DMF). Suitable electrophilic reagents include alkyl halides, arylalkyl halides (i.e., benzyl chloride), carboxylic acid chlorides, alkyl chloroformates, aryl chloroformates, N,N-dialkylcarbamoyl chlorides, alkylsulfonyl chlorides, arylsulfonyl chlorides, alkyl chlorothioformates

(i.e., ClCOR)

and aryl chlorothioformates

(i.e., ClCOAr)

SCHEME X

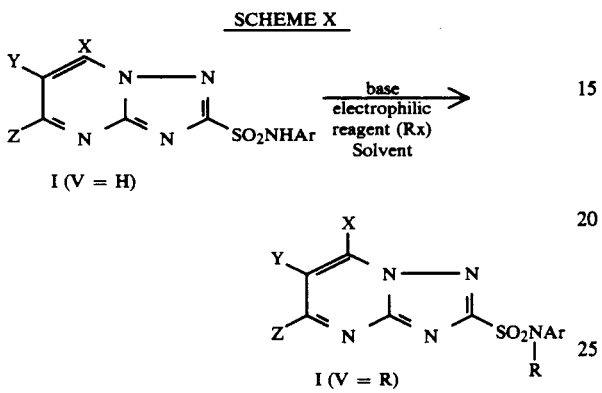

Agriculturally acceptable salts of the compounds of Formula I can be prepared by treatment of compounds of Formula I with a metal hydroxide such as sodium hydroxide, potassium hydroxide, or magnesium hydroxide, or an amine such as ammonia, dimethylamine, triethylamine, triethanolamine, diallylamine, 2-butoxyethylamine, morpholine, cyclododecylamine, or benzylamine. The reactions are typically carried out in a solvent in which one or more of the compounds of Formula I, the base, and the agriculturally acceptable salt product has appreciable solubility. Water is a preferred solvent. The agriculturally acceptable salts can be recovered from the reaction mixtures obtained by conventional means such as filtration or evaporation of the volatile components, or the reaction mixtures can be used without isolation.

In typical operations, a compound of Formula I is placed in water or other suitable solvent and an approximately equimolar quantity or an excess of base is added. The solution obtained is combined with agriculturally acceptable adjuvants and used as a herbicide.

The salts of this invention are additionally useful for purifying the compounds of Formula I. In typical operations, a contaminated compound of Formula I is combined with an excess of base in water to obtain a solution of the salt. Water insoluble contaminants are then removed by filtration or extraction with an immiscible organic solvent, such as methylene chloride or ether, and the compound of Formula I is regenerated by the addition of an acid and recovered by filtration, centrifugation, or the like. Sodium hydroxide and ammonium hydroxide are preferred bases and hydrochloric acid a preferred acid in these procedures.

Compounds of the present invention represented by Formula II are also derived from compounds represented by Formula I as illustrated in Scheme XI. The general process involves the reduction of compounds of general Formula I with an appropriate reducing agent in a suitable solvent to yield compounds of general Formula II. Reducing agents which are effective include metal hydrides (i.e., sodium borohydride) in the presence of acids (i.e., methanesulfonic acid) and hydrogen in the presence of a normal hydrogenation catalyst (i.e., palladium on carbon). For reductions with metal hydrides, polar aprotic solvents (i.e., DMSO) are most frequently used. For reductions using hydrogen and a catalyst, alcohols (i.e., ethanol) are most frequently employed as solvents.

SCHEME XI

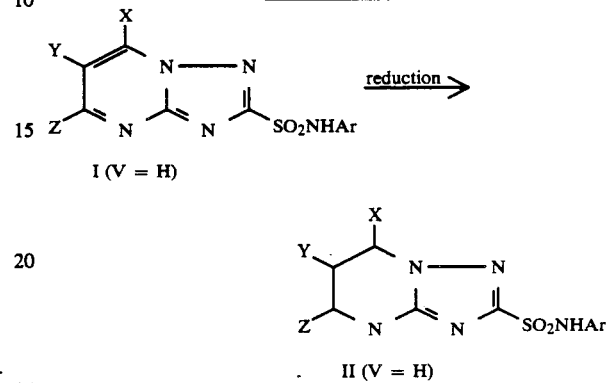

The majority of the amino compounds (ArNH$_2$) utilized to prepare the compounds of the present invention as illustrated in Scheme I were obtained from commercial sources or prepared by known literature procedures or minor modifications of literature procedures. Others are novel compounds made by novel processes.

A number of the amino compounds (ArNH$_2$) used to prepare the compounds of the present invention are derivatives of anthranilic acid. Many of these compounds can be prepared according to conventional methods described by S. J. Holt et al., Royal Soc. Proc. Sec. B, 148, 481 (1958), P. W. Sadler et al., J. Am. Chem. Soc., 78, 1251 (1956), and G. Reissenweber et al., U.S. Pat. No. 4,310,677 (1982). Other anthranilic acid derivatives can be prepared by standard derivatizations (i.e., conversion to esters and amides) of known substituted or unsubstituted 2-nitrobenzoic acids followed by reduction of the nitro group as represented in Scheme XII.

SCHEME XII

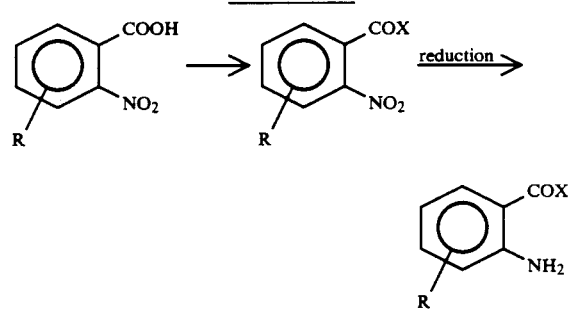

X = alkoxy, amino or alkylamino

A number of the amino compounds are prepared by reduction of anthranilic acids or esters and subsequent derivatization of the reduction product. This is outlined in Scheme XIII. The carbinol reduction products may be derivatized by reaction with base and various electrophiles (i.e., alkyl halides and carboxylic acid chlorides).

SCHEME XIII

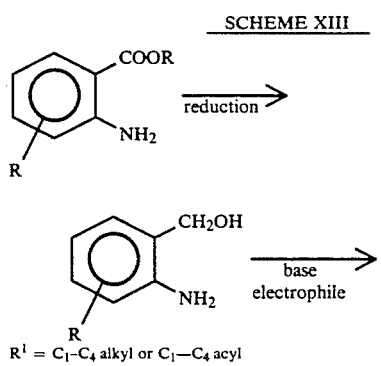

$R^1 = C_1-C_4$ alkyl or $C_1-C_4$ acyl

A large number of the amino compounds utilized in the preparation of the compounds of this invention contain halogen substituents ortho to the amino group. Many of these compounds were prepared by halogenation of the corresponding material bearing no substituent in the ortho position according to a general procedure described by R. S. Neale et al., *J. Org. Chem.*, 29, 3390 (1964). The starting materials for these halogenations are commercially available or known in the literature (i.e., British Patent No. 695,164 (1953); D. S. Noyce et al., *J. Org. Chem.* 26, 1732 (1961) and U.S. Pat. No. 3,813,234 (1974)). In certain instances to facilitate the transformation and insure ortho selectivity in the halogenation process the starting materials for the halogenation were acetamide derivatives (ArNHCOCH$_3$) or derivatives containing groups (i.e., Br) which would block halogenation at other positions in the molecule (i.e., para to the amino group). Following halogenation the acetamide derivatives were hydrolized back to the desired amino compound and the blocking groups were removed (i.e., Br in the para position was selectively removed by reduction in the presence of Cl in the ortho position). Other chlorine and bromine substituted amino compounds were prepared by known procedures (i.e., U.S. Pat. No. 4,188,342 (1980); C. R. Rasmussen et al. *J. Med. Chem.*, 21, 1044 (1978); H. E. Dadswell et al. *J. Chem. Soc.*, 1102 (1927); U.S. Pat. No. 3,813,234 (1974) and P. B. D. DeLaMare and J. H. Ridd, "Aromatic Substitution, Nitration and Halogenation", Academic Press, New York (1959), p. 106.

A number of the amino compounds used as starting materials for the compounds of this invention contain sulfur substituents in the ortho position. These were prepared using known procedures (i.e., R. R. Gupta et al *Heterocycles*, 16, 1527 (1981)and J. P. Chupp et. al., *J. Org. Chem.*, 49 4711 (1984)). In some cases alkylthio groups were present and these were synthesized by alkylation of the corresponding mercaptan. Compounds having alkyl or aryl sulfinyl or sulfonyl groups were synthesized by oxidation of the appropriate alkyl or arylthio groups.

Some starting amino compounds containing amino, alkylamino, aryloxy or pyridyloxy groups were prepared by catalytic reduction of the corresponding nitro compounds. The amino, alkylamino, aryloxy or pyridyloxy group were usually introduced via displacement of a leaving group ortho to the nitro group in the requisite nitrobenzene.

Other starting amino compounds were prepared by procedures involving metalation of the aromatic ring of N-substituted derivatives (i.e., t-butoxycarbonyl derivatives) of an aromatic amino compound followed by the resulting organometallic reagent with an electrophile. This general procedure is described in H. Gschwend, *Org. Reactions*, Vol. 20, 1-360 (1979) and is outlined in Scheme XIV. Suitable metalating agents are organolithium reagents (i.e., n-butyl lithium or t-butyl lithium). Typical electrophiles include alkyl halides (i.e., methyl iodide, ethyl iodide), aldehydes (i.e., formaldehyde, acetaldehyde), ketones (i.e., acetone), alkyl or aryl sulfonyl halides (i.e., methylsulfonyl chloride), and dialkyl or diaryl disulfides (i.e., dimethyl disulfide). These electrophiles are useful for the introduction of alkyl, hydroxyalkyl and alkylthio or arylthio groups to the position ortho to the amino group. After the reaction of the organometallic intermediate with the electrophile the nitrogen substituent is removed by hydrolysis.

SCHEME XIV

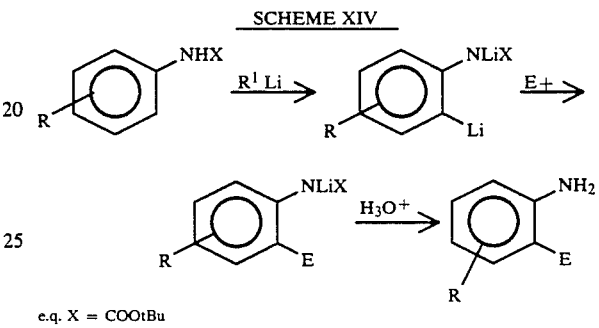

e.q. X = COOtBu

Other aromatic amino compounds used to prepare compounds of the present invention are prepared by conversion of carboxylic acid groups or derivatives of carboxylic acid groups to amino groups by standard methodology. Such a transformation is illustrated in Scheme XV and described in *J. Royal Netherlands Chem. Soc.*, 97, 53 (1978)

Scheme XV

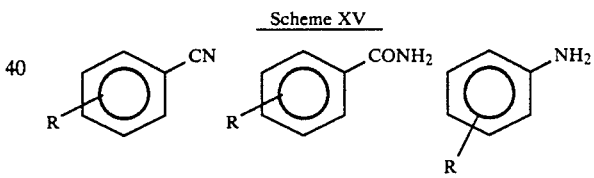

Other amino compounds such as those which are heteroaromatic amino compounds are prepared by known procedures such as those described in *Rec. Trav. Chim.*, 69, 673 (1950), T. Talik et al., *Chem. Abstracts*, 59: 8698a (1963) and L. C. Behr and R. Fusco In "*Heterocyclic Compounds*", A. Weissberger, Ed. Vol 22, Interscience Publishers, New York (1967), pp. 3-174 or straightforward modification of the art described above.

Other amino compounds used to prepare compounds of the present invention are prepared by direct metalation of the aromatic ring. This is illustrated schematically in Scheme XVI. An aromatic ring bearing one to three substituents on the ring may be metalated with an alkyl lithium reagent (i.e. n-butyl lithium, s-butyl lithium or t-butyl lithium) to form an aryl lithium intermediate. This reaction is most frequently, carried out in an ethereal solvent (i.e. diethyl ether, tetrahydrofuran or 1,2-dimethoxyethane) at temperature ranging from 78° C. to ambient temperature. It is sometimes advantageous to perform the metalation reaction in the presence of additives such as tetramethylethylyenediamine. The aryl lithium reagent is generated in situ and is reacted with carbon dioxide followed by protonation of the resultant carboxylate to form the carboxylic acid. The carboxylic acid can then be converted to the corresponding amino compound by standard methodology of the Hoffman, Curtius, Lossen and Schmidt reactions.

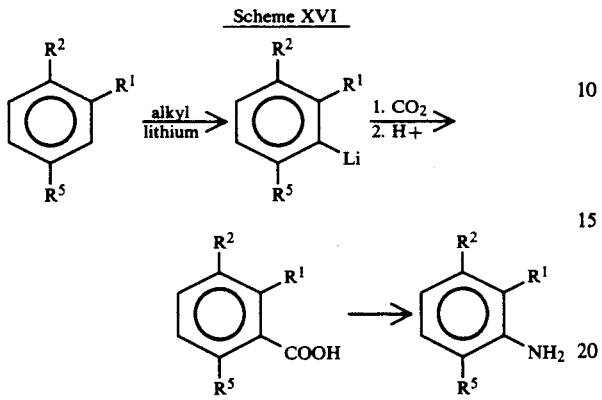

Scheme XVI

The substituents ($R^1$, $R^2$, and $R^5$), which are operable in the process illustrated in Scheme XVI are as follows: $R^1$, $R^2$, and $R^5$ may be chosen from among H, F, Cl, Br, I, $C_1$-$C_4$ alkyl, $C_1$-$C_4$ mono- or polyhaloalkyl or $C_1$-$C_4$ alkoxy. Most preferred substituents are $R^2$ is equal to H or $C_1$-$C_4$ alkyl; $R^1$ and $R^5$ are equal to F, Cl, $C_1$-$C_4$ mono- or polyhaloalkyl or $C_1$-$C_4$ alkoxy.

The intermediate carboxylic acid formed as illustrated in Scheme XVI or derivatives of the carboxylic acid (i.e. esters and amides) can be utilized to prepare other amino compounds which are useful in the preparation of compounds of Formula I of the present invention. This process is illustrated in Scheme XVII. When the carboxylic acid product contains a leaving group such as a F, Cl or Br atom at an adjacent position, the carboxylic acid may be converted to a suitable derivative and the halogen may then be replaced by displacement with a suitable nucleophile. Nucleophiles which are useful in this case include ammonia, $C_1$-$C_4$ monoalkylamines, $C_1$-$C_4$ dialkylamines, $C_1$-$C_4$ alkali metal alkoxides, $C_1$-$C_4$ alkali metal mono- or polyhaloalkoxides or $C_1$-$C_4$ alkali metal mercaptides. The use of these nucleophiles serves to replace the halogen substituent with amino, $C_1$-$C_4$ monoalkylamino, $C_1$-$C_4$ dialkylamino, $C_1$-$C_4$ alkoxy, $C_1$-$C_4$ mono- or polyhaloalkoxy or $C_1$-$C_4$ alkylthio respectively. The resultant products of the nucleophilic displacement can be converted to the corresponding amino compound by standard methodology of the Hoffman, Curtius, Lossen and Schmidt reactions.

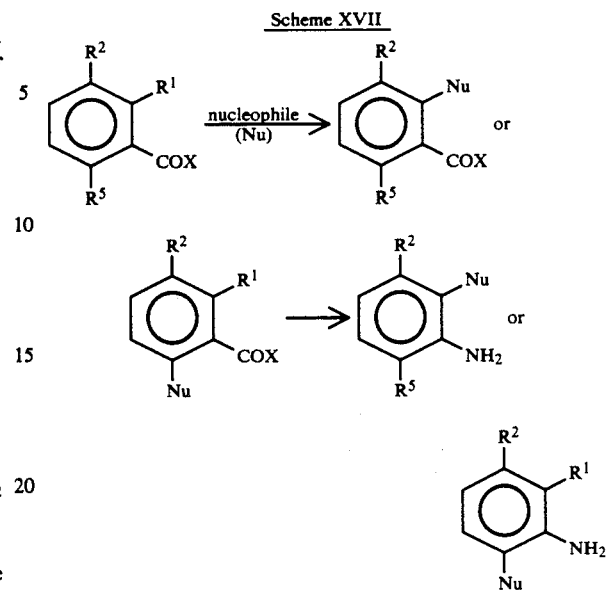

$R^1$ or $R^3$ = halogen and X = OH, OR*, or N(R*)$_2$ where R* = H or $C_1$-$C_4$ alkyl.

Other amino compounds which are useful in the preparation of compounds of Formula can be prepared as illustrated in Scheme XVIII. The starting material for this procedure is 2,6-difluoroaniline. The amino group of the aniline is protected with a silyl protecting group according to a general procedure described by Magnus et al. in *Tetrahedron Lett.*, 1787 (1981) and Guggenheim et al. in *Tetrahedron Lett.*, 1253 (1984). The protected aniline can then be metalated with an alkyl lithium reagent (i.e. n-butyl lithium, s-butyl lithium or t-butyl lithium) to form the corresponding aryl lithium reagent. The metalation is best carried out in ethereal solvents such as diethyl ether, tetrahydrofuran or dimethoxyethane at temperatures ranging from −78° C. to ambient temperature. It is sometimes advantageous to carry out the metalation in the presence of additives such tetramethylethylenediamine. The aryl lithium reagent is formed in situ and can be reacted with a variety of electrophilic reagents such as $C_1$-$C_4$ alkyl halides, $C_1$-$C_4$ dialkyl disulfides or $C_1$-$C_4$ alkyl sulfenyl halides. di-methylformamide, $C_1$-$C_4$ acyl halides or $C_1$-$C_4$ N-methyl-O-methyl alkylhydroxamates, $C_1$-$C_4$ alkyl chloroformates and carbon dioxide. These electrophilic reagents serve to introduce $C_1$-$C_4$ alkyl, $C_1$-$C_4$ alkylthio, formyl, $C_1$-$C_4$ acyl, $C_1$-$C_4$ alkoxycarbonyl and carboxyl groups, respectively, directly into the 3-position of the aromatic ring. The product from electrophilic substitution can be deprotected using standard methodology as described in the literature to form the desired amino compound.

Scheme XVIII

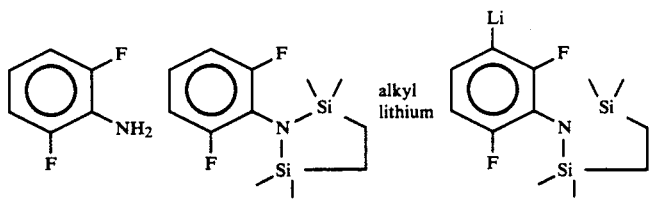

Scheme XVIII

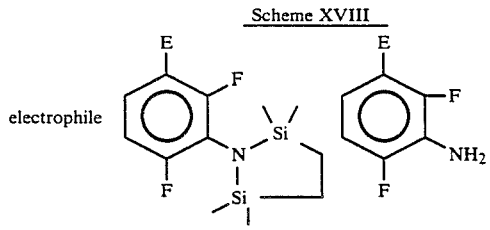

The table which follows contains a listing of some of the aromatic amino compounds prepared by methods described above and not previously described in known art, which compounds are useful in the preparation of the biologically active compounds of this invention.

wherein (1) $R^1$ represents $CF_3$, $R^2$ represents hydrogen, and $R^5$ represents $C_1$-$C_4$ alkoxy, $C_1$-$C_4$ polyfluoroalkoxy, or $C_1$-$C_4$ alkylthio; (2) $R^1$ and $R^5$ represent F and $R^2$ represents $CH_3$ or $OCH_3$; (3) $R^1$ and $R^5$ represent Cl and represents $CO_2C_1$-$C_4$ alkyl, or $CF_3$; (4) $R^1$ repre-

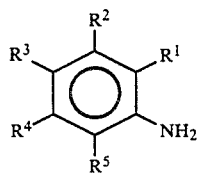

| Compound | $R^1$ | $R^2$ | $R^3$ | $R^4$ | $R^5$ |
|---|---|---|---|---|---|
| A | Cl | COOCH₃ | H | H | Cl |
| B | Br | COOCH₃ | H | H | CH₃ |
| C | CH₃ | Cl | H | H | COOCH₃ |
| D | Cl | CF₃ | H | H | Cl |
| G | Cl | H | H | H | CH₂OCH₃ |
| H | Cl | H | H | H | CH₂OAc |
| I | Cl | H | H | H | CH₂OCH₂Ph |
| J | 4-CF₃-2-Cl-phenoxy | H | H | H | H |
| K | 5-CF₃-2-pyridyloxy (3-Cl) | H | H | H | H |
| L | 4-CF₃-2-Cl-phenoxy | H | H | H | F |
| M | F | H | H | H | SCH₃ |
| N | CF₃ | H | H | H | OCH₃ |
| O | CF₃ | H | H | H | N(CH₃)₂ |
| P | CF₃ | H | H | H | OCH₂CH₃ |
| Q | CF₃ | H | H | H | OCH₂CF₃ |
| R | Br | CH₃ | H | H | Br |
| S | Br | CH₃ | H | H | Cl |

The novel aniline compounds that are useful for the preparation of compounds of Formulae I and II can be described by the formula

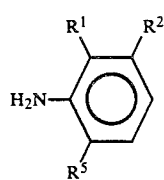

sents F, $R^2$ represents hydrogen, and $R^5$ represents $C_1$-$C_4$ alkylthio or 4-trifluoromethylphenoxy or 5-trifluoromethyl-2-pyridyloxy, each optionally containing up to two fluoro, chloro, or bromo substituents; (5) $R^1$ represents Cl, $R^2$ represents hydrogen, and $R^3$ represents hydroxymethyl, $C_1$-$C_4$ alkoxymethyl, $C_1$-$C_4$ alkanoyloxymethyl, or benzyloxymethyl; (6) $R^2$ and $R^5$ represent hydrogen and $R^1$ represents 4-trifluoromethylphenoxy or 5-trifluoromethyl-2-pyridyloxy, each optionally containing up to two fluoro, chloro, or bromo substituents; (7) a $C_1$-$C_4$ alkyl 3-amino-2-bromo- 4-methylbenzoate; and (8) a $C_1$–$C_4$ alkyl 4-chloro-3-methylanthranilate.

Using the routes illustrated above or minor variations based on the principles illustrated above the novel compounds of this invention can be prepared.

The invention is further illustrated by the following examples.

EXAMPLE 1

Preparation of N-(2-methoxy-6-trifluoromethylphenyl)-5,7-dihydroxy-1,2,4-triazolo[1,5-a]pyrimidine-2-sulfonamide Sodium (5.90 g, 257 mmol) was added to 250 ml of absolute ethanol under nitrogen and allowed to react. A 28.67 g, 85.0 mmol sample of N-(2-methoxy-6-trifluoromethylphenyl)-5-amino-1,2,4-triazole-3-sulfonamide and 24.46 g (170 mmol) of dimethyl malonate were added and the mixture heated at reflux with stirring for two days. It was then cooled with an ice bath and the solids present were collected by filtration and washed with hexane. They were then dissolved in about 150 ml office water and acidified with conc. hydrochloric acid to obtain 11.95 g, the title compound, which was collected by filtration and dried. The ethanolic solution was concentrated by evaporation and dried by adding toluene and removing volatiles by evaporation under reduced pressure three times. The residue was taken up in ethanol and treated as before with sodium and 16.85 g of dimethyl malonate to obtain another 10.26 g of the title compound A total of 22.21 g (64.5 percent of theory) of the title compound, which melts at 237°–243° C. with decomposition, was obtained.

EXAMPLE 2

Preparation of N-(2-methoxy-6-trifluoromethylphenyl)-5,7-dichloro-1,2,4-triazolo[1,5-a]pyrimidine-2-sulfonamide A 2.03 g (5.0 mmol) sample of N-(2-methoxy-6-trifluoromethylphenyl)-5,7-dihydroxy-1,2,4-triazolo[1,5-a]pyrimidine-2-sulfonamide was combined with 15 ml of phosphorus oxychloride and the mixture heated to reflux with stirring for eight hours. The mixture was allowed to cool and the solids present were collected by filtration and washed with cold toluene. They were then washed with water and dried to obtain 0.55 g (24.9 percent of theory) of the title compound. This material was homogeneous by chromatography and its NMR spectrum was compatible with the assigned structure. Additional product was obtained by quenching the phosphorus oxychloride solution with ice water.

EXAMPLE 110

Preparation of 6-methoxy-2 trifluoromethylbenzoic acid

A solution of 3-trifluoromethylanisol (50.0 g, 0.28 mole) in tetrahydrofuran was cooled to −78° C. under nitrogen atmosphere with stirring. To this solution was added n-butyl lithium (114 ml of 2.5M, 0.28 mole), dropwise at such a rate that the temperature did not exceed −65° C. When the addition was complete, the mixture was stirred at −78° C. for three hours. The mixture was then poured over a slurry of dry ice/ether and allowed to come to room temperature. The solvent was removed under reduced pressure to give a white solid. This solid was dissolved in a minimum amount of water, extracted with diethyl ether (2×100 ml) and the aqueous phase was acidified to pH 2 with dilute hydrochloric acid. An oil formed and was extracted with diethyl ether, washed several times with water and dried over magnesium sulfate. The solvent was removed to give 45.6 g (74 percent of theory) of the title compound as a white solid of m.p. 129°–130° C.

Analysis: Calculated for $C_9H_7F_3O_3$: C, 49.11; H, 3.21. Found: C, 49.08; H, 3.21.

EXAMPLE 4

Preparation of 6-methoxy-2-trifluoromethylbenzamide

A mixture of 6-methoxy-2-trifluoromethylbenzamide (40.0 g, 0.18 mol) in thionyl chloride (50 ml, 0.48 mol) was heated under reflux for three hours. The formed hydrogen chloride was neutralized in an aqueous sodium hydroxide trap. When the evolution of hydrogen chloride stopped, the mixture was cooled to room temperature and the excess thionyl chloride was removed by evaporation under reduced pressure. The resulting acid chloride was added dropwise with vigorous stirring to 250 ml of 12N ammonium hydroxide while cooling to 0° C. in a salt/ice bath. When the addition was complete, the mixture was allowed to warm to ambient temperature and stir for an additional to hours. The solid that formed was collected by filtration, dried under vacuum and recrystallized from methylcyclohexane to give 32.4 g (82 percent of theory) of the title compound as a white solid of m.p. 178°–181° C.

Analysis: Calculated for $C_9H_8F_3NO_2$: C, 49.31; H, 3.68; N, 6.39. Found: C, 49.05; H, 3.79; N, 6.34.

EXAMPLE 5

Preparation of 6-methoxy-2-trifluoromethylaniline

Sodium hydroxide (4.6 g, 0.11 mol) was dissolved in 50 ml of water and the solution was cooled to 0° C. in a salt/ice bath. Bromine (5.87 g, 37 mmol) was slowly added to this solution and allowed to stir at 0° C. for 15 minutes. To this rapidly stirred solution was added in portions 6-methoxy-2-trifluoromethylbenzamide (6.4 g, 30.0 mmol) keeping the temperature below 5° C. The mixture was stirred at 0° C. for three hours and then heated to reflux for two hours. It was then allowed to cool to ambient temperature and was extracted with methylene chloride (2×100 ml). The organic phase was combined and dried over magnesium sulfate. The solvent was removed under reduced pressure and the resulting amber liquid distilled to give 4.1. g (71 percent of theory) of the title compound as a clear, colorless oil, b.p. 56° C. at 0.7 mm Hg.

Analysis: Calculated for $C_8H_8F_3NO$: C, 50,28; H, 4.22; N, 7.33. Found: C, 50.24; H, 4.12; N, 7.03.

EXAMPLE 6

Preparation of 2,6-difluoro-3-methylaniline

Sodium hydroxide (5.6 g, 0.14 mol) was dissolved in 50 ml of water and then cooled to 0° C. in a salt/ice bath. Bromine (9.60 g, 60.0 mmoles) was slowly added to this solution and allowed to stir at 0° C. for 15 minutes. To this solution was added in portions with rapid stirring 2,6-difluoro-3-methylbenzamide (7.0 g, 37.0 mmol) keeping the temperature below 5° C. The mixture was stirred at 0° C. for three hours and then heated to reflux for two hours. It was then allowed to cool to ambient temperature and was extracted with methylene chloride (2×100 ml). The organic phases were combined and dried over magnesium sulfate. The solvent was removed by evaporation under reduced pressure and the resulting amber liquid distilled to give the title compound a clear, colorless oil having a b.p. of 107° C. at 15 mm Hg and amounting to 2.1 g (36 percent of theory).

Analysis: Calculated for $C_7H_7F_2NO$: C, 52.84; H, 4.43; N, 8.80 Found: C, 52.59; H, 4.73; N, 8.97.

Representative 1,2,4-triazolo[1,5-a]pyrimidine-2-sulfomamide compounds preparable from 2,6-difluoro-3-methylaniline and 2-methoxy-6-(trifluoromethyl)aniline, respectively, include Compounds 140, 174, 190, 219, 230, 309, 335, 343, and 350 and Compounds 104, 120, 141, 175, 191, 223, 231, 318, 324, 330, 337, and 340 of U.S. Pat. No. 4,886,883, the descriptions of which are hereby incorporated by reference. Numerous examples illustrating the preparation of 1,2,4-triazolo-[1,5-a]pyrimidine-2-sulfonamide compounds related to these compounds and describing methods suitable for the preparation of these compounds are also given in U.S. Pat. No. 4,886,883 and are hereby incorporated by reference.

The compounds of the present invention are highly effective herbicides when applied to the locus of vegetation, herein defined as encompassing pre-emergent (soil) applications as well as post-emergent (foliar) applications. They have utility for broad spectrum pre- and/or post-emergence weed control in areas where complete vegetation control is desired. Certain of these compounds are effective for the control of nutsegde (cyperus spp.). The subject compounds are also useful for selective pre- and/or postemergence weed control in crops such as wheat corn, soybeans, rice, and cotton. While none of the compounds are selective for use in all crops, by all methods of application, and at all rates of application, each is active as a herbicide and most are selective for use in one or more crops at some application rates and by some methods of application. The data provided herein in the examples can be used as a guide in choosing appropriately selective compounds from the compounds of Formulae I and II, appropriate application methods, and appropriate application rates for controlling unwanted vegetation in various crops. It is well within the skill of those in the art to select appropriate compounds of Formulae I and II not mentioned in the examples using the information herein and routine procedures.

Certain of the compounds of Formula I, notably those wherein X and Z represent $C_1-C_4$ alkyl, are resistant to degradation in the environment and, therefore, have limited utility as selective herbicides in crops where crop rotation programs are practiced except where the soil and climate are especially favorable for degradation. These compounds, on the other hand, are particularly useful as industrial herbicides where multi-year control is desired.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat ® 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic® 61 (molecular weight about 1000), polyethylene glycol ester of tall oil acids, sodium octophenoxyethoxyethyl sulfate, tris(polyoxyethylene)sorbitan monostearate (Tween® 60), and sodium dihexylsulfosuccinate.

The herbicidally effective concentration of the active ingredients in solid or liquid compositions generally is from about 0.00003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including, for example, the substituted urea herbicides such as 3-(3,4-dichlorophenyl)-1,1-dimethylurea, 3-(3,4-dichlorophenyl)-1-methoxy-1-methylurea (Lorox®) and 1,1-dimethyl-3-($\alpha,\alpha,\alpha$-trifluoro-m-tolyl)urea (Cotoran®); the triazines such as 2-chloro-4-(ethylamino)-6-(isopropylamino)-s-triazine and 2-chloro-4-(1-cyano-1-methylethylamino)-6-ethylamino-s-triazine (Bladex®); the uracils such as 5-bromo-3-sec-butyl-6-methyluracil; N-(phosphonomethyl)glycine; the phenoxies such as 2,4-dichlorophenoxyacetic acid; picolinic acids such as 4-amino-3,5,6-trichloropicolinic acid (Tordon®) and 3,6-dichloropicolinic acid (Lontrel®); 4-chloro-2-butynyl-3-chlorophenyl carbamate (Carbyne®); diisopropylthiocarbamic acid, ester with 2,3-dichloroallyl alcohol (Avadex®); diisopropylthiocarbamic acid, ester with 2,3,3-trichloroallyl alcohol (Avadex® BVD); ethyl-N-benzoyl-N-(3,4-dichlorophenyl)-2-aminopropionate (Suffix®); 1,2-dimethyl-3,5-diphenylpyrazolium methylsulfate (Avenge®); methyl (2-[4-(2,4-dichlorophenoxy)phenoxy]propanoate) (Hoelon®); butyl 2-[4-[(5-(trifluoromethyl)-2-pyridinyl)oxy]phenoxy]propanoate (Fusilade®); esters of 2-[4-[(3-chloro-5-trifluoromethyl)-2-pyridinyl)oxy]phenoxy]propionic acid; 4-amino-6-tert-butyl-3-(methylthio)-1,2,4-triazin-5-(4H)-one (Lexone®); 3-isopropyl-1H-2,1,3-benzothiadiazin-(4)-3H-one 2,2-dioxide; $\alpha,\alpha,\alpha$-trifluoro-2,6-dinitro-N,N-dipropyl-p-toluidine; 1,1'-dimethyl-4,4'-bipyridinium ion; 2-chloro-2',6'-diethyl-(methoxymethyl)acetanilide; and 2-[1-(ethoxyimino)butyl]-5-[(2-ethylthio)propyl]-3-hydroxy-2-cyclohexen-1-one (Poast®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equally effective at similar concentrations or against the same plant species. In non-selective preemergence and foliar treatments, the active ingredients of the invention are usually applied at an approximate rate of from about 0.01 to about 10 pounds/acre. In pre- and postemergence operations for selective uses, a dosage of about 0.01 to about 10 pounds/acre is generally applicable, a rate of 0.01 to 4 pounds/acre being preferred.

The herbicidal utility of some of the 1,2,4-triazolo[1,5-a]pyrimidine-2-sulfonamide compounds preparable from 2,6-difluoro-3-methylaniline and 2-methoxy-6-(trifluoromethyl)aniline is described in Examples 118–121 of U.S. Pat. No. 4,886,883, which description is hereby incorporated by reference.

We claim:
1. The compound 2-methoxy-6-trifluoromethylaniline.
2. The compound 2,6-difluoro-3-methylaniline.

* * * * *